United States Patent [19]
Line et al.

[11] Patent Number: 6,010,695
[45] Date of Patent: *Jan. 4, 2000

[54] SACCHAROMYCES BOULARDII TREATMENT TO DIMINISH CAMPYLOBACTER AND SALMONELLA IN POULTRY

[75] Inventors: J. Eric Line; Norman J. Stern; J. Stan Bailey; Nelson A. Cox, all of Athens, Ga.

[73] Assignee: The United States of America, as represented by the Secretary of Agriculture, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/694,805

[22] Filed: Aug. 9, 1996

Related U.S. Application Data

[63] Continuation-in-part of application No. 08/282,580, Jul. 29, 1994, abandoned.

[51] Int. Cl.[7] .................................................. A01N 63/00
[52] U.S. Cl. ..................................... 424/93.51; 435/255.2
[58] Field of Search ................................ 435/255.2, 940, 435/942; 424/93.51

[56] References Cited

U.S. PATENT DOCUMENTS

| | | | |
|---|---|---|---|
| 545,887 | 10/1995 | Casas-Perez | 424/93.45 |
| 4,335,107 | 6/1982 | Snoeyenbos et al. | 424/93 |
| 4,657,762 | 4/1987 | Mikkola et al. | 424/93 |
| 5,722,342 | 3/1998 | Line et al. . | |

OTHER PUBLICATIONS

Bailey, S.J., 1993, Control of Salmonella and Campylobacter in poultry production. A summary of work at Russell Research Center. Poultry Science 72:1169–1173.

L.C. Blankenship et al., 1993. Two–step mucosal competitive exclusion flora treatment to dimish Salmonellae in commerical broiler chickens. Poultry Science 72:1667–1672.

H. Blehaut et al., 1989. Disposition kinetics of *Saccharomyces boulardii* in man and rat. Biopharmaceutics and Drug Disposition 10:353–364.

J.P. Buts et al., 1986. Response of human and rat small intestinal mucosa to oral administration *Saccharomyces boulardii*. Pediatric Research 20:192–196.

J.P. Buts et al., 1993. *Saccharomyces boulardii* for Clortridium difficile–associated enteropathies in infants. J. Pediatric Gastroenterology and Nutrition 16:419–425.

E.F. Caballero et al., 1993. Valor alimenticio de la levadura torula (Candida utilis) en dietas paraves. Vet. Mex. 24(2):145–147.

F. Castex et al., 1990. Prevention of Clostridium difficile–induced experimental pseudomembranous colitis by *Saccharmyces boulardii*: a scanning electron microscopic and microbiological study. J. Gen. Microbiol. 136:1085–1089.

G.W. Elmer et al., 1987. Supression by *Saccharomyces boulardii* of toxigenic Clostridium difficle overgrowth after vancomycin treatment in hamsters. Antimicrobial Agents and Chemotherapy 31(1):129–131.

F.T. Jones et al., 1991a. A survey of Salmonella contamination in modern broiler production. J. Food Protect. 54:502–507.

F.T. Jones et al., 1991b. A survey of Campylobacter jejuni contamination in modern broiler production and processing systems. J. Food Protect. 54:259–262.

J.E. Kvenberg et al., 1987. Economic impact of colonization control on foodborne disease. Food Technol. Jul. 1977–1981.

E. Nurmi et al., 1973. New aspects of Salmonella infection in broiler production. Nature 214:210–211.

J.S.Ooterom et al., 1983. Origin and prevalence of Campylobacter jejuni in poultry processing. J. Food Protect. 46:339–344.

V.G. Stanley et al, 1993. The use of saccharomyces cerevisiae to suppress the effects of aflatoxicosis in broiler chicks. Poultry Sci. 72:1867–1872.

S. Stavric et al., 1993. Undefined and defined bacterial preparations for the competitive exclusion of Salmonella in poultry—A review. J. Food Protect. 56:173–180.

N.J. Stern et al., 1992. Comparison of three methods for recovery of Campylobacter spp. from broiler carcasses. J. Food Protect. 55:663–666.

N.J. Stern, 1994. Mucosal Competitive exclusion to diminish colonization of chickens by Campylobacter jejuni. Poultry Science 73: pp. 402–407.

C.M. Surawicz et al, 1989a. Prevention of antibiotic–associated diarrrhea by *Saccharomyces boulardii*: a prospective study. Gastroenterology 96:981–988.

C.M. Surawicz et al. 1989b. Treatment of recurrent Clostridium difficile colitis with vancomycin and *Saccharomyces boulardii*. Am. J. Gastroenterology 84:1285–1287.

C.M. Surawicz et al., 1993. *Saccharomyces boulardii* prevents recurrent C. Difficile pseudomembranous colitis and diarrhea: a multicenter controlled trial. Gastroenterolgy 104:A786.

N.J. Stern et al., 1988. Colonization characteristics of Campylobacter jejuni in Chick Ceca. Avian Diseases 32:330–334.

L.V. McFarland et al., 1993. *Saccharomyces boulardii*: A review of an innovative biotherapeutic agent. Microbial Ecology in Health and Disease 6:157–171.

Kinney, M.B. et al; "Digestive Diseases and Sciences," vol. 35, #7, Jul. 1990, pp. 897–901.

Tronkinson et al., Poultry Sci. 44, 159–164, 1965.

Soncini, et al.,Archivio veterinario italiano, Apr. 30, 1978, vol. 29, No. 1/2, suppl., pp. 60–61.

*Primary Examiner*—Irene Marx
*Attorney, Agent, or Firm*—M. Howard Silverstein; John D. Fado; Gail E. Poulos

[57] ABSTRACT

A preparation of Saccharomyces strains is used for reducing colonization by human enteropathogenic bacteria in poultry. This is referred to as a defined competitive exclusion preparation. It is especially effective for both Salmonella and Campylobacter.

5 Claims, No Drawings

SACCHAROMYCES BOULARDII TREATMENT TO DIMINISH CAMPYLOBACTER AND SALMONELLA IN POULTRY

This application is a continuation of application Ser. No. 08/282,580, filed Jul. 29, 1994 now abandoned.

BACKGROUND OF THE INVENTION

1. Field of the Invention

This invention relates to a method for reducing the presence of human enteropathogenic bacteria in poultry.

2. Description of the Prior Art

The consumption of improperly prepared poultry products has resulted in numerous cases of human intestinal diseases. It has long been recognized that Salmonella spp. are causative agents of such diseases, and more recently Campylobacter spp., especially *Campylobacter jejuni*, has also been implicated. As many as two million cases of salmonellosis occur annually in the United States (Stavric et al., Journal of Food Protection, Volume 56, No. 2, 173–180, February 1993); twice as many cases of campylobacteriosis are thought to occur (Krienberg et al., Food Technology, pages 77, 80, 81, and 98, July 1987). Both microorganisms may colonize poultry gastrointestinal tracts without any deleterious effects on the birds and, although some colonized birds can be detected, asymptomatic carriers can freely spread the microorganisms during production and processing, resulting in further contamination of both live birds and carcasses. Poultry serves as the primary reservoir for Salmonella and Campylobacter in the food supply (Jones et al., Journal of Food Protection, Volume 54, No. 4, 259–262, April 1991; Jones et al., Journal of Food Protection, Volume 54, No. 7, 502–507, July 1991). The intestinal contents of chickens may harbor up to $10^7$ Campylobacter and/or Salmonella per gram, and cross contamination during processing is frequent (Oosterom et al., Journal of Food Protection, Volume 46, No. 4, 339–344, April 1983). Studies have demonstrated that fecal material constitutes the major source from which edible parts of chickens are contaminated in processing plants. Therefore, to significantly reduce the level of contamination on processed poultry, pathogen-free or nearly pathogen-free birds must be delivered to the processing plant, (Bailey, Poultry Science, Volume 72, 1169–1173, 1993).

Better control measures are needed to minimize the spread of these and other human enteropathogenic bacteria; and the most promising approach to achieve this end has been to decrease the incidence and level of colonization by these microorganisms in poultry gastrointestinal tracts. To date, the most effective means for controlling Salmonella colonization is competitive exclusion (CE). Although the exact mechanism of CE protection is unclear, it is likely to be influenced by factors such as pH, Eh, production of inhibitory substances such as $H_2S$, bacteriocins, fatty acids, and conjugated bile acids; competition for nutrients and receptor sites; and local immunity (Mead et al., Letters in Applied Microbiology, Volume 10, 221–227, 1990). Competitive exclusion treatment involves introduction of intestinal flora from pathogen-free adult birds into newly hatched chicks. A study by Nurmi et al. (Nature, Volume 241, 210–211, Jan. 19, 1973), first reported the use of the competitive exclusion technique. The reference discloses inoculation of 1 to 2 day old chicks by oral gavage with a 1:10 dilution of normal intestinal contents from healthy adult birds. One day later, the chicks were challenged with Salmonella. After 8–22 days, the birds were examined for the presence of Salmonella. It was found that only 33% of the treated birds were colonized with Salmonella whereas 100% of the untreated birds were colonized with Salmonella. Originally, a suspension of crop and intestinal tract materials obtained from healthy, adult birds was used. In later studies, cecal content was cultured anaerobically in a liquid medium. It was found that preparations of subcultured intestinal contents from healthy, adult birds conferred protection to young chicks whose intestinal or gut microflora had not yet been established. Administration of undefined CE preparations to chicks speeds up the maturation of the gut flora in the newly-hatched birds and also provides a substitute for the natural process of transmission of microflora from the adult hen to its offspring. Snoeyenbos et al., U.S. Pat. No. 4,335,107 (1982) developed a technique designed to reduce salmonellae in poultry where the source of CE microflora was lyophilized fecal droppings which were propagated by anaerobic culture. Mikkola et al., U.S. Pat. No. 4,657,762 (1987) discloses the use of intestinal fecal and cecal contents as a source of CE microflora. Treatment with their culture required media to be anaerobic and pH balanced. Neither of these CE treatments addressed Campylobacter.

Since CE was known to be effective against Salmonella, a similar method for the control of Campylobacter was investigated by Stern et al. (Avian Diseases, Volume 32, 330–334, 1988). It was found, however, that treatment with CE preparations such as described by Nurmi et al. (1973), Snoeyenbos et al. (1982) and Mikkola et al (1987), did not affect Campylobacter colonization. After treatment with five different CE cultures, colonization was observed after challenge by Campylobacter in 81 of 84 chicks, and 45 of 46 control chicks. Shanker et al. confirmed these observations (Epidemiol. Infect., Volume 104 101–110, 1990). Stern and Stern et al. (Poultry Science, Vol. 73, 402–407, 1994; and U.S. patent application Ser. No. 08/031,983, which are both herein incorporated by reference) disclose a mucosal competitive exclusion (MCE) method and preparation effective against Campylobacter and Salmonella, using an anaerobic culture of the mucin layer scraped from cecal epithelia and an anaerobic culture of a cut piece of the washed ceca. This undefined MCE culture contains a diversity of flora that successfully competes with Salmonella and diminishes levels of Campylobacter in the chick.

The treatments discussed above all relate to the use of undefined mixtures of organisms obtained from cecal contents or cecal wall scrapings which are subcultured. While these undefined cultures have generally proven to be effective in reducing colonization of chickens with foodborne pathogens, there are concerns regarding their safety since there is the possibility of transmission of etiological agents associated with human foodborne disease and/or the transmission of avian disease.

Because of the safety concerns and difficulties in standardizing the bacterial composition and/or efficacy of undefined CE cultures, there is a need to develop defined compositions which exhibit the potency of undefined culture in order to diminish the presence of human enteropathogenic bacteria in poultry. Stavric et al. (Journal of Food Protection, Volume 56, No. 2, 173–180, February 1993) disclose that the formulation of effective defined cultures is difficult because of insufficient knowledge of the underlying protective mechanism(s) and interactions between gut microflora. Furthermore, the reference discloses, there is a lack of a sound scientific basis for the selection of potentially protective strains. To date, defined cultures of single isolates of Clostridium spp., *Streptococcus faecalis*, Bifidobacterium spp., and *Bacteroides hypermegas* have been examined. Furthermore, preparations containing several strains of single species, such as Bacteroides spp., Bifidobacterium spp., and Escherichia spp. have also been evaluated. None of these CE preparations consistently protect chicks against Salmonella challenge. The reference states that there has been one report claiming mixtures of lactobacilli protect poultry against Salmonella colonization.

Stavric further reports that the use of probiotics containing one to eight bacterial strains of different genera failed to protect poultry against Salmonella, although the data is limited. Studies with larger numbers of bacterial strains from different genera have shown limited success. Therefore, it was surprising to find that the present invention, which is a defined CE preparation of yeast, reduced the populations of Gram-negative enteropathogenic Campylobacter and Salmonella in poultry.

SUMMARY OF THE INVENTION

It is, therefore, an object of the present invention to provide a defined competitive exclusion composition to reduce pathogen colonization in poultry.

Another object of the present invention is to provide a defined competitive exclusion composition which diminishes the presence of Campylobacter and Salmonella in poultry.

A further object of the present invention is to provide a method for reducing pathogen colonization in poultry.

A still further object of the present invention is to provide a method for diminishing the presence of Campylobacter and Salmonella in poultry.

Further objects and advantages of the invention will become apparent from the following description.

DETAILED DESCRIPTION OF THE INVENTION

The importance of enteric infections in humans has been increasingly well recognized over the last dozen years. The relationship of poultry contamination and human infection has, likewise, become well documented. The ability to diminish this health hazard by interventions at poultry processing plants is also well known. During broiler production and processing, fecal materials containing pathogens are transferred onto meat and persist into the food processing kitchens.

The application of yeasts as competitive exclusion microflora for the reduction of pathogen colonization in poultry has been discovered. It was surprising that different species and strains of Saccharomyces diminish the populations of gram-negative enteropathogenic bacteria such as Campylobacter and Salmonella. *S. boulardii* is a non-pathogenic yeast originally isolated growing on lychee fruit in Indochina in the 1920s (Surawicz et al., Gastroenterology, Volume 96, 981–988, 1989). Since 1962, it has been used in several countries to treat antibiotic-associated diarrhea in humans. It has been used widely in Europe and is under study in the United States for treatment of patients whose intestinal microflora has been compromised by intensive antibiotic therapy (Surawicz et al., American Journal of Gastroenterology, Volume 84, 1285–1287, 1989; Gastroenterology, Volume 104, A786, 1993). Often in these patients, antibiotic resistant pathogens take advantage of the lack of competing organisms and colonize the intestines causing severe and sometimes fatal diarrhea. Administration of *S. boulardii* prevents toxin formation by Gram-positive *Clostridium difficile* (Buts et al., Journal of Pediatric Gastroenterology and Nutrition, Volume 16, 419–425, 1993) and reduces the concentrations of several aetiological agents of diarrhea (McFarland et al., Microbial Ecology in Health and Disease, Volume 6, 157–171, 1993).

Conditions are quite different in the ceca of a chicken than in the intestines of a human since the presence of Salmonella and Campylobacter species does not often result in a diseased bird. There are several attributes of *S. boulardii* which indicate it has potential as a competitive inhibition composition in poultry. First *S. boulardii* is rather thermophilic with an unusual optimum growth temperature of 37° C. It therefore is able to withstand the higher body temperature of birds which is about 41.5° C. for chickens. Second, the yeast has been shown to survive gastric acid in the stomachs of mammals to reach the intestines (Bluehaut et al., Biopharmaceutics and Drug Disposition, Volume 10, 353–364, 1989), which indicates that it might survive passage through the crop, proventriculus, and gizzard of chickens to reach the intestines and ceca. Third, it has demonstrated antagonistic activity in vitro and in vivo against various bacterial pathogens (Elmer et al., Antimicrobial Agents and Chemotherapy, January 1987, pp. 129–131); and last, *S. boulardii* can survive either aerobically or anaerobically, potentially making the culture and administration of the organism easier and more reliable than anaerobic cultures.

The method of this invention is applicable to any avian animal whether domestic or wild and particularly to poultry that are raised for human consumption which could serve as carriers for the target pathogens. Poultry includes all domestic fowl raised for eggs or meat and includes chickens, turkeys, geese, ducks, pheasants, and the like.

The target pathogens include all human enteropathogenic bacteria capable of colonizing poultry. Of particular interest are Salmonella and Campylobacter species.

Yeast includes any species and strains of Saccharomyces such as *S. boulardii, S. cerevisiae, S. carlsbergensis, S. ellipsoideus, S. intermedius*, for example, and of particular interest are *Saccharomyces boulardii* and *S. cerevisiae*.

Poultry is treated by administering an effective amount of yeast. The yeast can be administered by oral gavage, in drinking water, in feed, by spraying newly hatched chicks with an aqueous suspension, or a combination of the above. Yeast treatment is most effective if administered as early and as frequently as possible. For example, an effective amount of yeast in an aqueous suspension, is sprayed on birds when they are 50–75% hatched, followed by completion of the incubation period. In chickens, for example, hatching trays can be removed from the hatching cabinet after the eggs have been incubated in a setter for 18 days and in a hatching cabinet for about 2.5 days, and each tray is sprayed so that each hatching chick and/or unhatched egg receives the yeast preparation. The hatching trays are then returned to the hatching cabinet to complete incubation.

After the birds hatch, an effective amount of yeast can be added to the birds' first drinking water and is left in place until all has been consumed. In chickens, for example, an approximately about 1:200 dilution of yeast is placed in 1-gallon drinker jars which are placed in a broiler house at a ratio of approximately 1 jar per 200 chickens. The jars are left in place until all the water has been consumed (approximately 4 hours), resulting in consumption of approximately about 10 ml of diluted yeast solution per chick.

Alternatively, the preparation may be effectively administered by adding approximately about 5% by weight of a freeze-dried or encapsulated yeast preparation to feed, injecting in ovo, spraying directly on chicks after all the chicks are pipped, or by administering through the farm water system.

The following examples are intended only to further illustrate the invention and are not intended to limit the scope of the invention as defined by the claims.

EXAMPLE 1

Preparation of the Yeast Competitive Exclusion Culture

*Saccharomyces boulardii* (s.b.), accession number ATCC 74012 has been redeposited under the provisions of the Budapest Treaty with the American Type Culture Collection on Sep. 27, 1995. The Accession Number is ATCC 74352. (10801 University Boulevard, Manassas, Va. 20110-2209). Accession number ATCC 74102 has been redeposited at the American Type Culture Collection (12301 Parklawn Drive, Rockville, Md. 20852-1776) on Sep. 27, 1995 under the Budapest Treaty as *Saccharomyces boulardii*, RCC, ATCC accession number 74352. ATCC accession number 74352 will be irrevocably and without restriction or condition released to the public upon issuance of a patent.

*Saccharomyces cerevisiae* (s.c.) is used as purified baker's yeast from Fleishmann, Fleishmann's RAPIDRISE yeast.

YEAST IN DRINKERS

One colony of yeast is inoculated per 10 ml of sabouraud dextrose broth (SDB, Difco, Detroit, Mich.) and cultured at 30° C. for 24 hours. Each 10 ml culture was poured into bottles containing SDB (500 ml each) and allowed to grow at 30° C. for 48 hours. The cultures were then pelleted by centrifugation at 1000×g for 10 minutes. Each culture is separately suspended in 2000 ml of water for drinker bottles.

YEAST GAVAGING SOLUTIONS

Eight petri dishes containing sabouraud dextrose agar (SDA, Difco, Detroit, Mich.) are surface swabbed with a cotton-tipped swab inoculated with either *S. boulardii* or *S. cerevisiae*. The cultures are incubated at 30° C. for 24 hours and each harvested with a cotton tipped swab into 6 ml of phosphate buffered saline (PBS). 0.2 ml of the solution were administered perorally to each chick with a rubber-tipped needle. The yeast solutions were enumerated by plating serial 10-fold dilutions onto SDA and colony forming units (CFU) determined.

YEAST IN FEED

Dried baker's yeast is mixed in the feed at 5% by weight. Baker's yeast is also mixed in the drinking water using 10 grams/2000 ml of water.

EXAMPLE 2

Test for Yeast Efficacy Against Campylobacter 50 day-of-hatch chicks were purchased from a local hatchery and placed in groups of 10 into 5 separate isolation units equipped with nipple drinkers and a filtered air supply. One group was given 0.2 ml of a *S. boulardii* preparation, as described above in Example 1, by oral gavage daily for seven days. A second group received *Saccharomyces cerevisiae* in the same manner. A third group received a freeze-dried preparation of *S. cerevisiae* mixed in feed to make a preparation of approximately about 5% yeast in feed. The fourth group received no treatment (positive control). The fifth group received no treatment (negative control). On day 5, each chick, except those in the negative control group, received, by oral gavage, approximately 3.2×10⁵ Campylobacter cells which was a mixture of three strains of Campylobacter originally isolated from chickens. In addition to daily gavage yeast treatment or feed supplement, the yeast was also added to the drinking water as described in Example 1. Stir plates were used to keep the yeast suspended as it was delivered through nipple drinkers to the chicks. On day 8, the chicks were killed by cervical dislocation and individually weighed. Their ceca were aseptically removed and placed in small stomacher bags. The ceca and contents were diluted 1:4 in phosphate-buffered saline and blended for 30 seconds. The suspensions were serially diluted and plated on CEFEX agar for recovery of Campylobacter spp. (Stern et al., Journal of Food Protection, Volume 55, 663–666, 1992, herein incorporated by reference). The plates were incubated under a microaerobic environment at 42° C. for 24 hours prior to enumerating Campylobacter colonies.

The results are presented in Table 1 below.

TABLE 1

DIMINISHED CAMPYLOBACTER COLONIZATION OF CHICKENS DUE TO YEAST TREATMENT

| Group Description | Mean Log Campylobacter/g | Difference, Positive Ctrl. | # Colonized Birds/10 |
| --- | --- | --- | --- |
| 1. S.b. gavage | 2.58 | 4.57 | 4 |
| 2. S.c. gavage | 5.29 | 1.86 | 8 |
| 3. S.c. 5% in feed | 4.82 | 2.33 | 7 |
| 4. Positive control | 7.15 | 0 | 9 |
| 5. Negative control | <10 | — | 0 |

A reduction in Campylobacter levels of 4.6 log was noted in chicks receiving *S. boulardii* by oral gavage as compared to chicks receiving no yeast treatment. Chicks receiving *S. cerevisiae* by oral gavage or in the feed showed reduced Campylobacter levels of 1.9 and 2.3 log respectively. Not only were the Campylobacter populations reduced, but, perhaps more importantly, the incidence of colonization was also reduced. Nine out of ten of the positive control birds were found to have Campylobacter in their ceca while only 4 out of the 10 birds receiving *S. boulardii* were contaminated by Campylobacter. The birds treated with *S. cerevisiae* also showed reduced incidence of Campylobacter.

EXAMPLE 3

Test for Yeast Efficacy Against Salmonella

Chickens were obtained as in Example 2 above (30, day-of-hatch) and placed in groups of 10 into three isolation units. Positive control, negative control, and a treatment group were designated. The treatment group received 0.2 ml of *S. boulardii* by daily oral gavage as described in Examples 1 and 2. Positive control and treatment groups were challenged on day two with approximately 1×10⁶ *Salmonella typhimurium* (with induced resistance for nalidixic acid) per bird. Daily yeast treatments as described above in Example 2 were continued until day 8 when the chicks were sacrificed and sampled as in Example 2. Salmonella colonization was determined by plating serial dilutions on brilliant green sulfa (BGS) agar containing nalidixic acid. Results are presented below in Table 2.

TABLE 2

DIMINISHED SALMONELLA COLONIZATION OF
CHICKENS DUE TO YEAST TREATMENT

| Group Description | Mean Log Campylobacter/g | Difference, Positive Ctrl. | # Colonized Birds/10 |
|---|---|---|---|
| 1. Positive control | 5.08 | 0 | 10 |
| 2. Negative control | <10 | — | 0 |
| 3. S.b. gavage | 3.36 | 1.72 | 7 |

A reduction in Salmonella colonization levels of 1.7 log was observed in chicks treated with S. boulardii as compared to the positive controls. The negative control birds showed no evidence of Salmonella contamination as expected. Furthermore, an increase in weight gain was observed in birds treated with yeast as compared to controls. The results are presented in Table 3 below.

TABLE 3

WEIGHT GAIN BY CHICKENS DUE TO YEAST TREATMENT

| Group Description | Mean Bird Weight (g) |
|---|---|
| 1. Positive control | 138.7 |
| 2. Negative control | 141.4 |
| 3. S.b. gavage | 147.5 |

If this weight gain persists through the life of the bird, another benefit of this treatment will be increased production.

The foregoing detailed description is for the purpose of illustration. Such detail is solely for that purpose and those skilled in the art can make variations therein without departing from the spirit and scope of the invention.

We claim:

1. A method for reducing levels of colonization of human enteropathogenic bacteria in poultry comprising administering a defined competitive exclusion preparation consisting of *Saccharomyces boulardii* ATCC 74352 in amounts effective to reduce levels of colonization of human enteropathogenic bacteria in poultry.

2. The method of claim 1 wherein said administering of said preparation is selected from the group consisting of administering in drinking water, administering in food, administering by spraying, and administering by oral gavage.

3. A method for reducing levels of colonization of human enteropathogenic bacteria in poultry comprising administering by oral gavage a defined competitive exclusion preparation consisting of *Saccharomyces boulardii* ATCC 74352 in amounts effective to reduce levels of colonization of human enteropathogenic bacteria in poultry.

4. The method of claim 3 wherein said preparation reduces colonization of Campylobacter in said poultry.

5. The method of claim 3 wherein said preparation reduces colonization of Salmonella in said poultry.

* * * * *

UNITED STATES PATENT AND TRADEMARK OFFICE
CERTIFICATE OF CORRECTION

PATENT NO. : 6,010,695
DATED : January 4, 2000
INVENTOR(S) : J. Eric Line, et al.

It is certified that error appears in the above-identified patent and that said Letters Patent is hereby corrected as shown below:

On the title page, item [73]:

Signed and Sealed this

Twenty-first Day of November, 2000

Attest:

Q. TODD DICKINSON

*Attesting Officer*       *Director of Patents and Trademarks*